US008357627B2

(12) United States Patent
Nariyuki et al.

(10) Patent No.: US 8,357,627 B2
(45) Date of Patent: Jan. 22, 2013

(54) DEODORIZING CATALYST, DEODORIZING METHOD USING THE SAME, AND METHOD FOR REGENERATING THE CATALYST

(75) Inventors: Akane Nariyuki, Hiratsuka (JP); Shinji Hashimoto, Hiratsuka (JP); Ryoji Aikawa, Hiratsuka (JP); Kenta Takeuchi, Hiratsuka (JP); Yuji Tozuka, Hiratsuka (JP)

(73) Assignee: Nikki-University Co., Ltd., Tokyo (JP)

( * ) Notice: Subject to any disclaimer, the term of this patent is extended or adjusted under 35 U.S.C. 154(b) by 0 days.

(21) Appl. No.: 13/003,659

(22) PCT Filed: Jul. 14, 2009

(86) PCT No.: PCT/JP2009/062712
§ 371 (c)(1),
(2), (4) Date: Feb. 22, 2011

(87) PCT Pub. No.: WO2010/007978
PCT Pub. Date: Jan. 21, 2010

(65) Prior Publication Data
US 2011/0136656 A1 Jun. 9, 2011

(30) Foreign Application Priority Data

Jul. 14, 2008 (JP) ................................. 2008-182587
Sep. 19, 2008 (JP) ................................. 2008-240433

(51) Int. Cl.
*A61L 9/01* (2006.01)
*B01J 23/34* (2006.01)
*B01J 23/745* (2006.01)
*B01J 38/00* (2006.01)

(52) U.S. Cl. ................ 502/324; 502/338; 422/4; 422/5

(58) Field of Classification Search .................. 502/324, 502/338
See application file for complete search history.

(56) References Cited

U.S. PATENT DOCUMENTS
5,266,543 A * 11/1993 Matsumoto et al. ............ 502/66

FOREIGN PATENT DOCUMENTS
JP  H08-243383  9/1996
JP  H09-276379  10/1997
JP  H10-099690  4/1998

(Continued)

OTHER PUBLICATIONS

Soong et al. Prepr. Pap. Am. Chem. Soc., Div. Fuel Chem., 37(1), 192-9, 1992.*

(Continued)

*Primary Examiner* — Vu A Nguyen
(74) *Attorney, Agent, or Firm* — Fish & Richardson P.C.

(57) ABSTRACT

A deodorizing catalyst showing high activity at room temperature, having great adsorption capacity, and possessing activity persistence capable of withstanding continued use; a deodorizing method using the catalyst; and a method for regenerating the catalyst are provided.
The deodorizing catalyst is characterized by containing manganese oxide and a Mn—Fe complex oxide at a weight ratio in the range of 98:2 to 60:40. A honeycomb catalyst having the catalyst carried thereon is also disclosed. The deodorizing method is characterized by treating a gas containing odor components with the catalyst. The method for regenerating the catalyst involves heating the catalyst to 140 to 250° C.

19 Claims, 5 Drawing Sheets

FOREIGN PATENT DOCUMENTS

| | | |
|---|---|---|
| JP | H10-137591 | 5/1998 |
| JP | H10-180108 | 7/1998 |
| JP | 2001-038207 | 2/2001 |
| JP | 2002-346374 | 12/2002 |
| JP | 2005-237997 | 9/2005 |
| JP | 2006-255251 | 9/2006 |
| JP | 2006-326272 | 12/2006 |
| JP | 2008-104845 | 5/2008 |

OTHER PUBLICATIONS

International Search Report.

* cited by examiner

DEODORIZING CATALYST, DEODORIZING METHOD USING THE SAME, AND METHOD FOR REGENERATING THE CATALYST

TECHNICAL FIELD

This invention relates to a deodorizing catalyst for removing odor components or harmful components, which are contained in air, at a relatively low temperature ranging from ordinary or room temperature to 100° C.

BACKGROUND ART

As methods for removing malodor components or harmful components in air, technologies different in action have hitherto been known, such as physical adsorption by activated carbon or zeolite, reactive absorption by reactive compounds, combustion by precious metal-based catalysts, chemical adsorption and decomposition by manganese oxide-based catalysts, degradation by photocatalysts, and oxidatively decomposing catalysts utilizing ozone. Of them, manganese oxide-based catalysts do not use expensive precious metals, do not require accessory equipment such as heating means or ozone generation means, and are economical. Thus, they are adopted in many fields.

Numerous catalysts containing manganese oxide as an active ingredient have been introduced. It has been introduced that as complex oxides composed of manganese and metals, Mn—Fe complex oxides, for example, exhibit a deodorizing action on acetaldehyde in a low temperature region of 50 to 200° C. (see Patent Document 1).

A deodorizing catalyst containing a manganese-iron complex oxide ($MnFe_2O_4$) as an active ingredient has been introduced. As a concrete example, a deodorizing catalyst containing a mixture of a Mn—Fe complex oxide (Mn/Fe element ratio is 33:67) and $Fe_2O_3$ (notes: the Mn/Fe element ratio of the mixture is explicitly described as 17:83) as an active ingredient is disclosed. It is described that the Mn—Fe complex oxide may be mixed with a manganese oxide to constitute the deodorizing catalyst, but there is no relevant Example, and there is no detailed description of such a catalyst (see Patent Document 2). A prototype of the catalyst composed of the mixture of a Mn—Fe complex oxide and $Fe_2O_3$ was built, and its deodorization performance was evaluated. The outcome turned out to be that the deodorization performance was not fully satisfactory.

As a deodorizing catalyst containing manganese oxide and zeolite, a deodorizing catalyst having manganese dioxide and a copper oxide carried on hydrophobic zeolite having a silica/alumina ratio of 100 or more has been shown to exhibit high deodorizing properties even for a high-humidity gas (see Patent Document 3).

A deodorizing catalyst containing active manganese dioxide and high silica zeolite as an active ingredient has been shown to adsorb a malodorous gas derived from sulfur and oxidatively decompose it (see Patent Document 4).

Furthermore, a deodorizing catalyst comprising a powdery manganese oxide and powdery hydrophobic zeolite in mixture has been shown to decompose odor components oxidatively at low temperatures (see Patent Document 5).

A deodorizing catalyst containing a manganese oxide, graphite, and zeolite is disclosed. In this catalyst, the proportion of the zeolite contained is 1 to 1.5 times that of the manganese oxide, and a composition having a Mn—Fe complex oxide mixed with MnO is not described (see Patent Document 6).

A deodorant containing a complex oxide of Mn and a transition metal, which contains potassium (K), concretely, a complex oxide obtained from $K_2CO_3$ (5%), CuO (20%) and $MnO_2$ (75%), has been introduced as accelerating the conversion of an aldehyde into a carboxylic acid (see Patent Document 7).

CITATION LIST

Patent Documents

Patent Document 1: JP-A-10-180108
Patent Document 2: JP-A-2001-38207
Patent Document 3: JP-A-8-243383
Patent Document 4: JP-A-10-137591
Patent Document 5: JP-A-2005-237997
Patent Document 6: JP-A-10-99690
Patent Document 7: JP-A-2006-255251

SUMMARY OF INVENTION

Technical Problem

For example, the smell of tobacco contains acetaldehyde and acetic acid. Air at a nursing home or the like contains, in addition to aldehydes and acetic acid, composite odor components, such as ammonia and trimethylamine which are nitrogen-based components, and methyl mercaptan, hydrogen sulfide and sulfides which are sulfur-based odor components. Thus, a deodorizing catalyst is required to show performance in removing a plurality of components, as those in the smell of tobacco, at the same time.

A deodorizing catalyst for air within an automobile may be exposed to air at a temperature of 50° C. or higher occasionally, further 60 to 80° C., at the start of an engine in the summer season. Even under such conditions, improvements in overall deodorization performance are demanded, such as a higher deodorization speed, a lower minimum achievable concentration, and a greater adsorption capacity. An even more desirable catalyst is one whose deteriorated adsorbing action can be regenerated.

An object of the present invention, therefore, is to provide a deodorizing catalyst whose deodorization speed is high, which can remove odor components or harmful components until extremely low concentrations are reached (in other words, minimum achievable concentrations are low), whose adsorption capacity is very great, and which can be regenerated. The deodorizing catalyst of the present invention is designed to remove one of or a plurality of these odor components or harmful components for a long term at a temperature of room temperature to 100° C.

Another object of the present invention is to provide a honeycomb catalyst which is excellent in deodorization performance during high speed treatment, which involves a small pressure loss, and which is reduced in noise.

Still another object of the present invention is to provide a deodorizing catalyst which is free from secondary pollution, namely, occurrence of an offensive odor due to desorption, and which, upon heating, easily decomposes adsorbed components into $CO_2$, thereby restoring catalytic activity; and to provide a method for regenerating the catalyst.

Solution to Problem

To attain the above objects, the inventor accomplished the following invention, whose aspects are as follows:

(1) A first aspect of the invention is a deodorizing catalyst composition comprising manganese oxide (component 1) and a complex oxide of manganese and iron (component 2) at a weight ratio of 98:2 to 60:40. By forming a deodorizing catalyst composition having this formulation, a deodorizing catalyst dramatically improved in the deodorization speed, the deodorization rate, the minimum achievable concentration, and the adsorption capacity can be realized. Even at a temperature of the order of 100° C., moreover, adsorbed odor components are not desorbed, so that an offensive odor due to desorption does not occur. Upon heating to 130° C. or higher, preferably 150° C. or higher, complete recovery of deodorizing power can be achieved.

(2) A second aspect of the invention is the deodorizing catalyst composition according to (1) above, wherein the weight ratio between the component 1 and the component 2 is 98:2 to 70:30. By setting this weight ratio, a deodorizing catalyst further improved in the deodorization speed, the deodorization rate, and the adsorption capacity can be realized.

(3) A third aspect of the invention is the deodorizing catalyst composition according to (1) or (2) above, wherein the average coordination number of Mn—O [N(Mn—O)] of the mixture of the component 1 and the component 2 is 6.5 to 7.5. By setting the Mn—O average coordination number in the above range, a deodorizing catalyst markedly high in the deodorization speed, the deodorization rate, the minimum achievable concentration and the adsorption capacity can be realized.

(4) A fourth aspect of the invention is the deodorizing catalyst composition according to any one of (1) to (3) above, further comprising zeolite (component 3), and wherein the weight ratio of the total amount of the component 1 and the component 2 to the amount of the component 3 is 90:10 to 50:50. By forming a mixture of zeolite as the component 3, the component 1 and the component 2, a deodorizing catalyst even higher in the deodorization speed and the adsorption capacity can be realized.

(5) A fifth aspect of the invention is the deodorizing catalyst composition according to (4) above, wherein the component 3 is zeolite having a $SiO_2/Al_2O_3$ molar ratio of 3 to 100. The resulting catalyst provides an excellent deodorization speed.

(6) A sixth aspect of the invention is the deodorizing catalyst composition according to (4) or (5) above, wherein the component 3 is one or more of MFI-type zeolite, β-type zeolite, and mordenite-type zeolite. By adopting this composition, a deodorizing catalyst excellent in the adsorption capacity and the deodorization speed can be realized.

(7) A seventh aspect of the invention is the deodorizing catalyst composition according to any one of (1) to (6) above, further comprising potassium (component 4). By adopting this composition, a deodorizing catalyst excellent in the adsorption capacity and the deodorization speed can be realized.

(8) An eighth aspect of the invention is the deodorizing catalyst composition according to (7) above, wherein the content of the component 4, expressed based on an oxide ($K_2O$), is 0.1 to 3% by weight with respect to the sum of the component 1 and the component 2. By incorporating potassium in this range, the effects of potassium are exhibited more effectively.

(9) A ninth aspect of the invention is the deodorizing catalyst composition according to (7) or (8) above, wherein the component (4) is incorporated by impregnating particles of at least one of the component 1 and the component 2 with a solution of a potassium compound, and then drying the impregnated particles at a temperature of 250° C. or lower, thereby impregnating the particles of at least one of the component 1 and the component 2 with the potassium compound or potassium oxide. By performing this method to provide a potassium-containing composition, a deodorizing catalyst, which contains potassium as a constituent of the complex oxide, can be realized to show the effects of potassium more effectively than do conventional deodorizing catalysts.

(10) A tenth aspect of the invention is the deodorizing catalyst composition according to (9) above, wherein the potassium compound is one or more compounds selected from inorganic acid salts, organic acid salts, and hydroxides. By impregnating the composition with this compound, the effects of potassium are exhibited more effectively.

(11) An eleventh aspect of the invention is the deodorizing catalyst composition according to any one of (1) to (10) above, adapted to remove one or more components to be deodorized, among acetaldehyde, tobacco smell components, formaldehyde, acetic acid, ammonia, volatile organic nitrogen compounds, hydrogen sulfide, and volatile organic sulfur compounds. The catalyst composition of the present invention makes it possible to realize a catalyst which exhibits the effect of simultaneously removing a plurality of odor components.

(12) A twelfth aspect of the invention is a method for producing the deodorizing catalyst composition according to any one of (7) to (10), comprising: a step 1 of impregnating mixed particles, which contain the component 1 and the component 2 at a weight ratio in the range of 98:2 to 60:40, with a solution of a potassium compound; and a step 2 of drying the impregnated mixed particles at a temperature of 250° C. or lower. This method can obtain a deodorizing catalyst composition or a deodorizing catalyst having the effects described in (7) to (9) above.

(13) A thirteenth aspect of the invention is a deodorizing catalyst having the deodorizing catalyst composition according to any one of (1) to (11) above carried on a catalyst substrate. The catalyst can be provided in a shape suitable for the conditions applied, and the catalyst can find wide varieties of uses.

(14) A fourteenth aspect of the invention is the deodorizing catalyst according to (13) above, wherein the catalyst substrate is a honeycomb substrate having a cell density of 50 to 100 cell/square inch, and which has the deodorizing catalyst composition according to any one of (1) to (11) above carried on the substrate as a catalyst layer in an amount of 200 to 500 g/L. By selecting the cell density of the honeycomb used and the amount of the catalyst composition carried on the honeycomb, and using the thus prepared deodorizing catalyst of the present invention, the maximum efficiency of deodorization can be achieved, with a pressure loss being suppressed, even during treatment of a large amount of a gas.

(15) A fifteenth aspect of the invention is a method for producing the deodorizing catalyst according to (13) or (14) above, comprising: a step 1 of coating the catalyst substrate with a slurry containing the component 1, the component 2 and a potassium compound; and a step 2 of drying the coated catalyst substrate at a temperature of 250° C. or lower.

(16) A sixteenth aspect of the invention is a method for producing the deodorizing catalyst according to (13) or (14) above, comprising: a step 1 of coating the catalyst substrate with a slurry containing the component 1 and the component 2; a step 2 of impregnating the coated catalyst substrate with a solution of a potassium compound; and a step 3 of drying the impregnate catalyst substrate at a temperature of 250° C. or lower.

(17) A seventeenth aspect of the invention is a deodorizing method, comprising passing air, as an object to be treated, through the deodorizing catalyst according to (13) or (14) above at a flow velocity of 0.5 to 4.0 m/second, the air containing one or more of acetaldehyde, tobacco smell components, formaldehyde, acetic acid, ammonia, volatile organic nitrogen compounds, hydrogen sulfide, and volatile organic sulfur compounds. By using the deodorizing catalyst of the present invention and setting the above gas velocity, deodorization can be carried out at a high speed and with efficiency.

(18) An eighteenth aspect of the invention is a method for regenerating a deodorizing catalyst composition, comprising: heating the deodorizing catalyst composition according to any one of (1) to (11) above to 140° C. to 250° C. in an air atmosphere, the deodorizing catalyst composition having adsorbed thereto one or more of acetaldehyde, tobacco smell components, formaldehyde, acetic acid, ammonia, sulfur compounds, and organic nitrogen compounds, which are odor components. The deodorizing catalyst composition of the present invention is heated to the above temperature, whereby its deodorization performance can be restored at a rate of 100% or nearly 100%. Thus, the deodorizing catalyst composition can be used for a long term.

(19) A nineteenth aspect of the invention is a method for regenerating a deodorizing catalyst, comprising: heating the deodorizing catalyst according to (13) or (14) above to 140° C. to 250° C. in an air atmosphere, the deodorizing catalyst having adsorbed thereto one or more of acetaldehyde, tobacco smell components, formaldehyde, acetic acid, ammonia, sulfur compounds, and organic nitrogen compounds, which are odor components. The deodorizing catalyst of the present invention is heated to the above temperature, whereby its deodorization performance can be restored at a rate of 100% or nearly 100%. Thus, the deodorizing catalyst can be used for a long term.

Advantageous Effects of Invention

According to the deodorizing catalyst of the present invention, the deodorization performance of a conventional deodorizing catalyst containing manganese oxide as an ingredient has been successfully improved markedly. The deodorizing catalyst of the present invention is dramatically high in deodorization speed and adsorption capacity, in particular, and can treat a large amount of a gas at a high speed. Thus, it can be downsized, and is free from the desorption of odor components which is liable to occur at restart of the engine. Consequently, a driver or a passenger can feel comfortable even in a high temperature vehicle.

DESCRIPTION OF EMBODIMENTS

Figure 1:
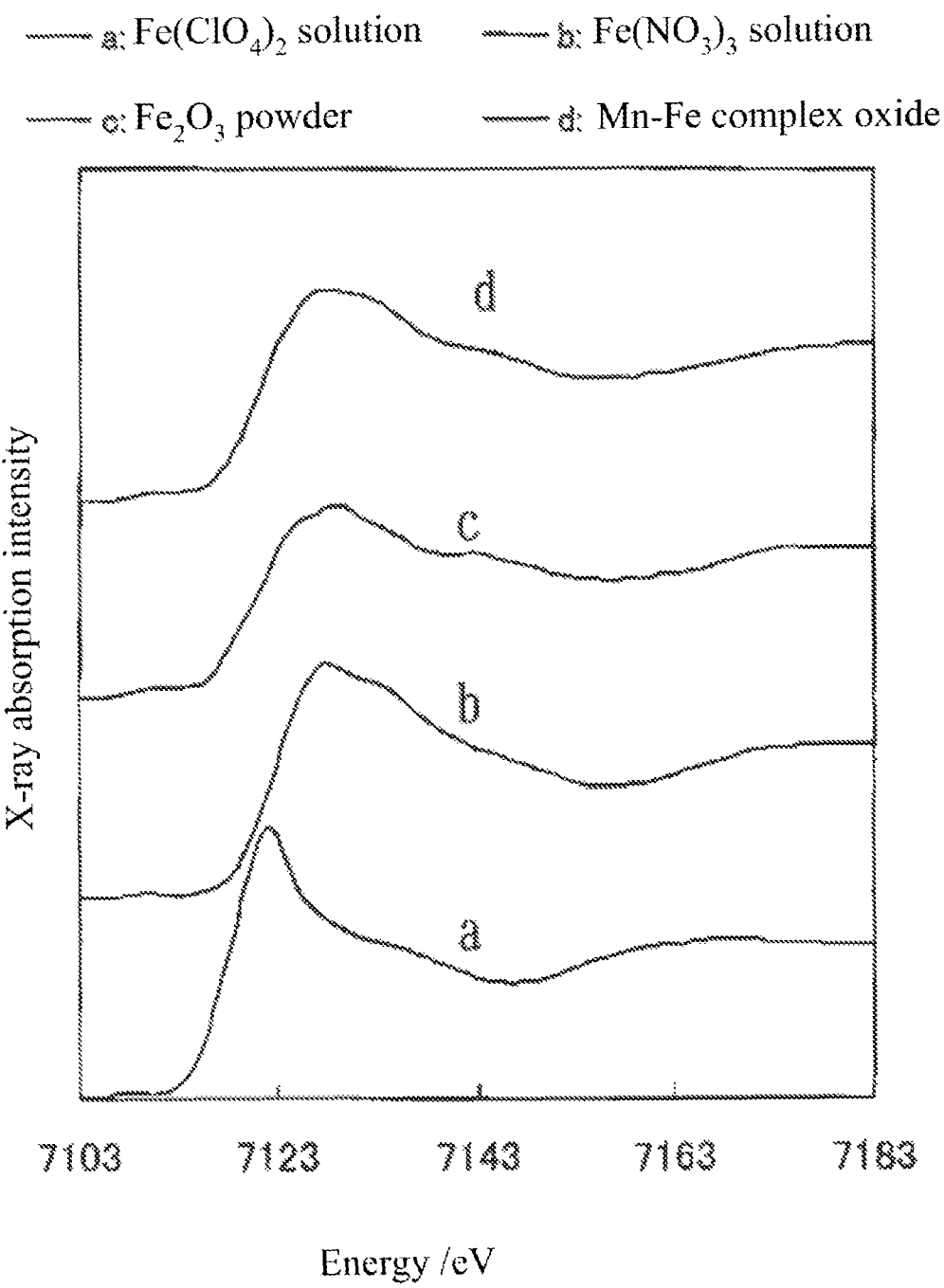
FIG. 1 shows the XANES spectrum of the Fe—K absorption edge of a Mn—Fe complex oxide.

The present invention will now be described in more detail below. In the following descriptions, a deodorizing catalyst composition refers to a mixture of catalyst components, and this composition processed in any of various shapes or supported or carried on any of various substrates or structures is expressed as a deodorizing catalyst.

The deodorizing catalyst composition of the present invention is composed of a formulation containing manganese oxide (component 1) and a complex oxide of manganese and iron (hereinafter referred to as Mn—Fe complex oxide) (component 2), and containing the component 1 and the component 2 at a weight ratio of 98:2 to 60:40. The catalyst composition of the present invention, comprising the component 1 and the component 2 in mixture, exhibits excellent deodorization performance. For example, a deodorizing catalyst composed of a component 1/component 2 mixture (weight ratio 95:5 to 80:20) shows deodorization performance, expressed as an acetaldehyde removal rate which is about 2 to 3 times as high as that of a deodorizing catalyst composed of the component 1 (100%), and adsorption capacity for acetaldehyde which is about 5 to 10 times as great as that of the latter deodorizing catalyst.

A formulation with even higher overall deodorization performance, expressed as deodorization speed, deodorization achievable concentration, and adsorption capacity, has a component 1/component 2 weight ratio of 98:1 to 60:40, preferably 98:2 to 70:30, more preferably 98:2 to 80:20, particularly preferably 95:5 to 85:15. A composition containing the component 2 in a proportion comparable to or higher than that of the component 1 exhibits only deodorization performance close to or lower than that of a deodorizing catalyst composed of the component 1 alone or the component 2 alone.

Component 1: Manganese Oxide

Manganese oxide, as the component 1 used in the present invention, is preferably porous particles having a large specific surface area, and called active manganese dioxide generally used as a raw material for a catalyst. Concretely, it is manganese oxide represented by the compositional formula $MnO_x$ ($0.9 \leq x \leq 2.1$). The average oxidation number of the manganese contained is not limited, but typically, is 2.5 or more, preferably 2.9 or more, but 4.1 or less. As for the physical properties, porous manganese oxide having an average particle diameter of 0.1 μm to 500 μm (a value by the laser diffraction scattering method) and a specific surface area (BET adsorption process) of 50 $m^2/g$ or more, more preferably 100 to 500 $m^2/g$, is preferred in order to increase the points of contact with particles of the component 2, and enhance the adsorption of components to be treated, as well as improve the contact efficiency by an increase in the gas contact area. The manganese oxide usable is, for example, that synthesized during a process in which an alkali compound is added to an aqueous solution of a $Mn^{2+}$ manganese compound such as manganese nitrate, and a $Mn^{7+}$ manganese compound such as potassium permanganate, to form a precipitate, drying it, and then firing it at 400 to 500° C. in air; or manganese dioxide for a catalyst which is generally marketed.

Component 2: Mn—Fe Complex Oxide

Mn—Fe complex oxide, as the component 2 used in the present invention, is preferably one having a ratio of the number of the atoms of Fe to the total number of the atoms of Mn and Fe, namely, [Fe]/([Mn]+[Fe]), which fulfills the value of 0.3 to 0.8. Its typical example is $MnFe_2O_4$ containing trivalent Fe. If the ratio of the number of the atoms falls short of the above range, the proportion of Fe in the complex oxide lowers, and accordingly, the average coordination number of Mn—O in the mixture with the component 1 decreases. This brings about the unfavorable result that the effect of enhancing deodorization performance is not sufficiently exhibited.

Thus, the lower limit of the element ratio is 0.3 or higher, preferably 0.4 or higher. If the above range is exceeded, on the other hand, the proportion of Mn in the complex oxide lowers. A catalyst produced using such a complex oxide cannot supply oxygen fully, and thus oxidation performance cannot be fully exhibited. For this reason, the preferred element ratio is 0.8 or lower, preferably 0.7 or lower.

The Mn—Fe complex oxide can be produced by the coprecipitation method. That is, an aqueous solution or a water-alcohol mixed solution containing a manganese compound and an iron compound at a stoichiometric ratio, for example, is prepared, and an aqueous solution of an alkali compound is added to this aqueous solution, thereby forming a coprecipitate containing Mn and Fe. The resulting coprecipitate is separated by filtration, washed with water to remove the excess alkali compound and residual salts, then dried at a temperature of the order of 100 to 150° C., and then heat-treated (fired) at 500 to 1000° C. in air, whereby the desired Mn—Fe complex oxide can be obtained. As the manganese compound and iron compound as the materials used, water-soluble compounds can be used, such as chlorides, nitrates, sulfates, or acetates. Examples of the alkali compound usable are ammonia, sodium hydroxide, potassium hydroxide, and sodium carbonate. The ratio of the number of the atoms of the complex oxide, [Fe]/([Mn]+[Fe]), can be arbitrarily adjusted to 0.3 to 0.8 by setting the materials in the desired proportions. To produce a Mn—Fe complex oxide having a [Mn]:[Fe] ratio of 1:2, for example, it suffices to compound the materials such that the proportion of iron (III) nitrate is 2 mols per mol of manganese (II) nitrate.

Solids of the resulting Mn—Fe complex oxide are adjusted to particles having an average particle diameter of 0.1 µm to 500 µm, preferably 0.1 µm to 100 µm, by pulverization and sifting means, and these particles are used as a component of the catalyst composition of the present invention.

Mixture of Component 1 and Component 2

In connection with catalyst compositions in which the proportions of the manganese oxide as the component 1 and the Mn—Fe complex oxide as the component 2 were varied, their deodorizing action was investigated. According to the results of this investigation, a formulation in which the average coordination number of Mn—O (expressed as [N(Mn—O)]) of the mixture of the component 1 and the component 2 was in the range of 6.5 to 7.5 was found to be dramatically increased in the removal rate for acetaldehyde and the adsorption capacity for acetaldehyde. The parameter [N(Mn—O)] was measured by the extended X-ray absorption fine structure (EXAFS) method, and represents the average coordination number of the closest oxygen around the manganese atoms. Thus, the deodorizing catalyst composition of the present invention has an average coordination number of Mn—O ([N(Mn—O)] of 6.5 to 7.5. The deodorizing catalyst composition with [N(Mn—O)] in the range of 6.5 to 7.5 can be obtained by mixing the component 1 and the component 2 at a weight ratio of 98:2 to 60:40, preferably 98:2 to 70:30, more preferably 95:5 to 70:30.

Method for Producing Deodorizing Catalyst Composition

The deodorizing catalyst composition of the present invention can be produced by mixing particles of the component 1 and particles of the component 2, which have been prepared beforehand, at a weight ratio of 98:2 to 60:40, as mentioned above.

Another preferred method for production is to disperse particles of the Mn—Fe complex oxide in a solution of materials for preparation of manganese oxide, and then convert the materials into manganese oxide. More specifically, the method comprises a step 1 of dispersing particles of a Mn—Fe complex oxide, as the component 2, in an aqueous solution of a $Mn^{2+}$ manganese compound, say, manganese nitrate, and a $Mn^{7+}$ manganese compound, say, potassium permanganate, which are materials for preparation of manganese oxide, and then adding aqueous ammonia or an aqueous solution of sodium hydroxide or the like to the dispersion, thereby precipitating a manganese oxide precursor as a precipitate; and a step 2 of separating the precipitate together with the Mn—Fe complex oxide particles, then washing the separated substances with water, then drying them at 100 to 150° C., and then firing them at 350 to 600° C., thereby preparing manganese oxide from the precursor. By this method, a homogeneous mixture of the component 1 and the component 2 can be produced.

Embodiment of Catalyst Composition

Another preferred embodiment of the catalyst composition of the present invention is a composition incorporating zeolite, as component 3, in addition to the above-mentioned component 1 and component 2. That is, the composition is a deodorizing catalyst composition containing manganese oxide (component 1) and a Mn—Fe complex oxide (component 2) at the above weight ratio, i.e., 98:2 to 60:40, preferably 98:2 to 70:30, especially 98:2 to 80:20, particularly preferably 95:5 to 85:15, and further containing zeolite (component 3) such that the ratio of the total amount of the component 1 and the component 2 to the amount of the component 3 (weight ratio) is 90:10 to 50:50, preferably 80:20 to 50:50. The deodorizing catalyst of the present invention containing the component 3 in the above range relative to the component 1 and the component 2 is further improved in deodorization speed and adsorption capacity, and is capable of removing VOC substances such as benzene and toluene. The proportion of the component 3 in excess of the above range is not preferred, because the deodorization speed lowers, and the time taken to reach 100% removal lengthens.

Component 3: Zeolite

Zeolite, as the component 3 used in the present invention, may be a natural product or a synthetic product. As the structural type, MFI type zeolite, β type zeolite, mordenite type zeolite, or Y type zeolite is preferred. Of them, the MFI type zeolite is particularly preferred in improving the deodorization speed. The molar ratio between $SiO_2$ and $Al_2O_3$, which are constituents of the zeolite, is 3 to 200, preferably 3 to 100, more preferably 5 to 95. Zeolite having such a molar ratio is preferred for increasing the removal speed. Zeolite comprising zeolite particles having an average particle diameter of 1 to 500 µm (value by the laser diffraction scattering method) is preferred, because it uniformly mixes with other components and increases contact properties.

Component 4: Potassium

Furthermore, other preferred embodiments of the deodorizing catalyst composition of the present invention are the following compositions containing potassium as component 4:

A deodorizing catalyst composition containing manganese oxide (component 1) and a Mn—Fe complex oxide (component 2) at a weight ratio in the range of 98:2 to 60:40, preferably 98:2 to 70:30, especially 98:2 to 80:20, particularly preferably 95:5 to 85:15, and further containing potassium (component 4) relative to this formulation.

A deodorizing catalyst composition containing manganese oxide (component 1), a Mn—Fe complex oxide (component 2) and zeolite (component 3), the weight ratio between the component 1 and the component 2 being as defined above, the zeolite (component 3) being contained such that the ratio of the total amount of the component 1 and the component 2 to the amount of the component 3 (weight ratio) is 90:10 to 50:50, and further containing potassium (component 4).

The content of the component 4, as an oxide, is 0.1 to 3% by weight, preferably 0.2 to 2.5% by weight, more preferably 0.5 to 2.0% by weight, based on the sum of the component 1 and the component 2. By this measure, the removal speed and the adsorption capacity for aldehydes are further improved. If the content of potassium exceeds 3% by weight, on the other hand, these properties decline. If it is 5% by weight or more, the adsorption capacity decreases.

In the catalyst composition of the present invention, the component 4 is present in the form of potassium oxide ($K_2O$), a potassium-containing inorganic salt, a potassium-containing organic acid salt, or a potassium hydroxide. The component 4 is also assumed to be present in a state in which it is deposited on the surfaces of the particles of the component 1 or the component 2, or within the pores of the particles, namely, in an impregnated state. In other words, the component 4 is not present in the state of chemical bonding to the component 1 or the component 2, for example, as a K—Mn—Fe complex oxide. The form of existence of the component 4 will be understood from the following description of a manufacturing method.

The catalyst composition of the present invention, which contains potassium, preferably has a potassium compound contained in particles of manganese oxide as the component 1, or particles of the Mn—Fe complex oxide as the component 2, or their mixed particles, by the following method:

Advisably, particles of at least one of the component 1 and the component 2 are impregnated with a solution of the potassium compound, and then the impregnated particles are dried. Concretely, the catalyst composition of the present invention can be produced by either heating the impregnated particles at a temperature of 100 to 250° C., preferably 130 to 250° C. to evaporate water and dry the particles, or forming potassium oxide to incorporate potassium into particles of the component 1 and/or particles of the component 2, and mixing both types of particles in the aforementioned proportions.

Potassium (K) as the component 4 included in the catalyst composition of the present invention is not contained in a form taken up into crystals of the manganese oxide as the component 1 or crystals of the Mn—Fe complex oxide as the component 2, but is existent such that the impregnated potassium compound or the potassium oxide formed by heating at 100 to 250° C. is deposited on the surfaces of or within the pores of the particles of the component 1 or the component 2 (that is, the particles are in the impregnated state).

The deposition of the potassium compound onto the catalyst composition (namely, the impregnation of the catalyst composition with the potassium compound) may be performed by a process for supporting or carrying on a catalyst substrate such as a honeycomb. That is, the following methods are shown by way of example:

A method comprising: a step 1 of coating the catalyst substrate with a slurry containing the component 1, the component 2 and the potassium compound; and a step 2 of drying the coated catalyst substrate at a temperature of 250° C. or lower, preferably 200 to 100° C.

A method comprising: a step 1 of coating the catalyst substrate with a slurry containing the component 1 and the component 2; a step 2 of impregnating the coated catalyst substrate with a solution of a potassium compound; and a step 3 of drying the impregnate catalyst substrate at a temperature of 250° C. or lower, preferably 200 to 100° C.

The potassium compound used to incorporate potassium into the catalyst composition of the present invention is exemplified by one or more compounds selected from inorganic acid salts such as $K_2CO_3$ and $KNO_3$, organic acid salts such as potassium acetate and potassium oxalate, and hydroxides. However, these compounds need not be limitative. Potassium permanganate is inferior in effects to the above-mentioned $K_2CO_3$, or is ineffective.

If the particles of the component 1 or component 2 impregnated with the potassium compound are heated at a higher temperature, for example, fired at a temperature of 400 to 600° C., catalytic performance declines. This is not desirable. With a K—Mn—Fe complex oxide containing potassium between the layers, the effect of incorporating potassium is not exhibited. The same can be said of manganese oxide having potassium incorporated therein by firing.

Actions

The reason why the deodorizing catalyst composition of the present invention containing the component 1 and the component 2 exhibits dramatically enhanced deodorization performance has not been elucidated clearly at present. However, the following reason is assumed, if acetaldehyde is taken as an example for illustration: Upon contact with acetaldehyde, the acetaldehyde is oxidized by Mn of the component 1 and, at the same time, the Mn itself is reduced. On the other hand, Fe contained in the Mn—Fe complex oxide as the component 2 takes in oxygen from air. The oxygen taken in oxidizes the Mn of the component 1 again, thereby dramatically improving the oxidative decomposition ability of the Mn. Also, the resulting carboxylic acid is chemically adsorbed or chemisorbed by the manganese oxide as the component 1. The chemisorption ability of manganese oxide can be maximized by setting the ratio between the component 1 and the component 2 (weight ratio) at 98:2 to 60:40.

The deodorizing catalyst composition of the present invention is used after being processed in a form suitable for practical uses or use conditions. For example, clay or the like is added to the catalyst composition, and the mixture is granulated to form particles or granules having a diameter of the order of 1 mm to 1 cm, or the catalyst composition is carried or supported on a carrier such as alumina or activated carbon particles, and the so prepared particles or granules or supported catalyst composition are or is filled into a bag of an unwoven fabric or the like as a filter, or alternatively, the catalyst composition of the present invention is supported, as a catalyst layer, on a catalyst substrate such as a honeycomb body or a foamed metallic body, and put to use. However, these forms are not limitative.

Honeycomb Catalyst

The deodorizing catalyst composition of the present invention has a high deodorizing power, and has a great adsorption capacity. Thus, it is particularly suitable for a honeycomb catalyst. To deodorize a large volume of air by the catalyst of a limited size in a short time, it is necessary to minimize a pressure loss and ensure a deodorization rate. For this purpose, there is need to optimize a combination of the cell density of the honeycomb, the catalytic performance, and the amount of the catalyst carried.

The honeycomb catalyst of the present invention is as follows:

(a) On a honeycomb substrate having a cell density of 50 to 100 cells/square inch, (b) the catalyst composition of the present invention (c) is supported or carried in an amount of 200 to 500 g/L (called the amount . . . carried) per liter of the honeycomb to form a catalyst layer.

The honeycomb substrate used preferably in the honeycomb catalyst of the present invention has a cell density of 50 to 100 cells/square inch, preferably 50 to 90 cells/square inch, more preferably 70 to 90 cells/square inch. The honeycomb substrate having the cell density less than this range provides an insufficient deodorization rate. A high density honeycomb substrate having the cell density in excess of the above range involves too great a pressure loss, and tends to decrease in the deodorization rate.

By setting the amount of the catalyst composition carried at a value in the range of 200 to 500 g/L, the deodorization rate can be kept high, with an increase in the pressure loss being curtailed. If the amount carried falls short of this range, the deodorization rate lowers. The parameter in excess of this range, on the other hand, tends to increase the pressure loss and decrease the deodorization rate. A more preferred amount carried for increasing the deodorization rate and decreasing the pressure loss is 250 to 500 g/L, more preferably 300 to 450 g/L. The amount carried (g/L) refers to the total weight of the component 1 and the component 2 constituting the catalyst composition of the present invention, or their total weight to which the component 3 is further added, and does not include the weight of a binder or the like.

As described above, the honeycomb catalyst of the present invention has a combination of (i) the deodorizing catalyst composition of the present invention, (ii) the specific honeycomb substrate, and (iii) the particular amount of the catalyst carried. Thanks to this combination, the honeycomb catalyst has dual performance, i.e., high speed deodorization and low pressure loss, such that it can achieve a one-pass removal rate of at least 20%, 25% or more, further 30% or more, even further 35% or more, for acetaldehyde at room temperature, and can decrease a pressure loss to less than 35 Pa, further 25 Pa or less (the lower limit is normally 10 Pa or above), even under high speed conditions under which the wind velocity of air to be treated is, for example, 3.5 m/second (corresponding to a space velocity SV of 830,000 hr$^{-1}$). As already explained, moreover, the honeycomb catalyst has excellent performance such that it shows activity at a temperature of room temperature to 100° C., and that it scarcely poses the problem of causing an offensive odor due to the desorption of the adsorbed components.

Production of Honeycomb Catalyst

The material for the honeycomb substrate for producing the honeycomb catalyst of the present invention may, for example, be suitably selected from corrugated or similar ceramics, metal foils of aluminum, stainless steel, titanium, etc., paper, glass fiber, and synthetic resins, but they are not limitative. A slurry containing the deodorizing catalyst composition of the present invention and a binder is coated on any of these materials by a publicly known method such as a spraying or dipping process. A surplus of the slurry is removed by applying pressurized air to adjust the amount of the catalyst composition carried to a proper amount. Then, the coated slurry is dried at 100 to 250° C., whereby a honeycomb catalyst is obtained. To produce a honeycomb catalyst containing potassium, there is adopted a method which comprises either allowing a potassium compound to be contained beforehand in particles of one or more of the component 1, the component 2 and the component 3 or contained beforehand in the slurry, or coating the slurry on the honeycomb substrate, and then impregnating the coated substrate with a solution of a potassium compound, followed by drying. As the binder, a silica sol, an alumina sol, or a resin-based binder is used as appropriate.

Purification of Air with Honeycomb Catalyst

The method of purifying air according to the present invention is to pass air, which contains odor components to be treated, through the honeycomb catalyst of the present invention at a temperature of room temperature to 100° C. or lower at a flow velocity of 4.0 m/second or less, preferably 3.5 m/second or less (the lower limit is not set, but the flow velocity is equal to or higher than the ordinary flow velocity, and concretely it is about 0.5 m/second or higher, from the point of view of attaining the purpose of air purification).

The deodorizing catalyst composition of the present invention or the deodorizing catalyst containing the composition exhibits an deodorizing action on acetaldehyde, formaldehyde, acetic acid, ammonia, sulfur compounds such as methyl mercaptan and hydrogen sulfide, and organic nitrogen compounds such as trimethylamine. Thus, air containing one or more of these compounds is brought into contact with the deodorizing catalyst of the present invention at a temperature of room temperature to 100° C. or lower, whereby the air can be deodorized. Moreover, the deodorizing catalyst of the present invention containing the component 3 exhibits a deodorizing action not only on the above-mentioned components, but also on volatile organic compounds (VOC) such as toluene, xylene and benzene. The concentration of these components differs according to the source of generation, but normally, is distributed in the range of 1 ppm to 1000 ppm. There are a case where only one component is contained, and a case where a plurality of components are contained. The deodorizing catalyst of the present invention can remove these respective components until they decrease to 0.2 ppm or less.

There are no special lower limits on the treatment temperature, as long as it is a temperature which enables the deodorizing catalyst of the present invention to function effectively. Thus, the room temperature refers to 0 to 25° C., but is not limited to this range.

Regeneration of Deodorizing Catalyst

The present invention provides a regeneration method for a deodorizing catalyst or the like, adapted to regenerate the catalyst of the present invention whose deodorizing function has declined, comprising heating the deodorizing catalyst composition or deodorizing catalyst having odor components adsorbed thereto, while flowing air therethrough, the temperature of the deodorizing catalyst or air flowed being raised to 140° C. or higher.

The deodorizing catalyst of the present invention, whose catalytic function has declined, is characterized by restoring its function nearly completely upon heating for 10 to 60 minutes at a temperature of 140° C. or higher, preferably 150 to 250° C., while air is flowing. Heating at a temperature of lower than 140° C. provides insufficient functional restoration, whereas heating at a temperature of higher than 250° C. results in a waste of energy. The deodorizing catalyst of the present invention has a very high deodorizing function after regeneration, and thus can be used repeatedly. When the catalyst of the present invention having acetaldehyde adsorbed thereto is heated in air, $CO_2$ begins to appear at about 130° C., and sharply increases at 140° C. or higher. The same profile is observed with acetic acid.

Field of Application

The deodorizing catalyst of the present invention is fast in the deodorization speed, extremely low in the minimum achievable concentration, and very great in the adsorption capacity. Thus, it can be applied to air purification in many fields, such as air cleaners and air conditioners for commercial use in hospitals, nursing homes, restaurants, and offices; air cleaners for passenger cars, rail cars, and airplane cabins; and exhaust treatment devices in factories and sewage treatment facilities.

EXAMPLES

Hereinbelow, the present invention will be described concretely by Examples and Comparative Examples, but these examples in no way restrict the scope of the present invention.

Example 1

Preparation of Mn—Fe Complex Oxide

A KOH aqueous solution (10% by weight) was gradually added to 300 cc of an aqueous solution having 70 g of iron nitrate (hexahydrate) and 58 g of manganese nitrate (hexahydrate) dissolved therein until the mixture reached pH 8. Then, stirring was continued for 1 hour to obtain a precipitate. After the precipitate was separated by a centrifugal separator, the precipitate was thoroughly washed with deionized water, and then dried for 2 hours at 150° C. in an air atmosphere. Then, the dried substance was fired in a muffle furnace for 3 hours at a temperature of 450° C. in the presence of air. The resulting cake of a Mn—Fe complex oxide was pulverized to obtain particles of the desired Mn—Fe complex oxide. The element ratio of Mn and Fe of the resulting complex oxide was subjected to fluorescent X-ray analysis, and was found to be 1:2. The oxidation number of Fe in the complex oxide was measured by a method to be shown below, and was found to be Fe(III).

Oxidation Number of Fe

A calibration was performed, with the energy value at the maximum value of the differentials of the XANES spectrum of an Fe metal being taken as 7111.2 eV. FIG. 1 shows the XANES (X-ray absorption near edge structure) region spectrum in the vicinity of the absorption edge of a spectrum obtained by subtracting a background from an XAFS spectrum measured for normalization, and reflects the electron status of the X-ray absorption element. The symbol (d) in FIG. 1 shows the spectrum of the Mn—Fe complex oxide prepared by the aforementioned method. FIG. 1 also shows, for purposes of comparison, the spectra of a divalent $Fe(ClO_4)_2$ solution (a in FIG. 1), a trivalent $Fe(NO_3)_3$ solution (b in FIG. 1), and $Fe_2O_3$ (c in FIG. 1). The energy position 7127 eV of the main peak of the present synthetic compound Fe—Mn complex oxide shifted rightward from the main peak of the divalent $Fe(ClO_4)_2$ solution by a value of the order of 6 eV, and was close to those of the trivalent $Fe(NO_3)_3$ solution and $Fe_2O_3$. That is, the oxidation number of Fe of the Mn—Fe complex oxide obtained in the above method was found to be trivalent.

<Preparation of Catalyst Compositions 1 to 8>

Manganese oxide ($MnO_2$) and a Mn—Fe complex oxide (expressed as $MnFe_xO_y$) were combined as in Table 1 to prepare catalysts 1 to 8.

<<Preparation of Catalyst 1>>

Potassium carbonate (3.5 g) was added to 1000 cc of an aqueous solution having 500 g of manganese carbonate dissolved therein, and the mixture was stirred for 1 hour to form a precipitate. The precipitate was separated by a centrifugal separator, then thoroughly washed with deionized water, and then dried for 2 hours at 150° C. Then, the dried substance was fired for 3 hours at 400° C., and then pulverized to obtain particles of $MnO_2$ having an average particle diameter of 2 µm and a specific surface area of 150 m²/g. These particles were designated as catalyst 1.

<<Preparation of Catalyst 2>>

The weights of the respective components were set so that the weight ratio between $MnO_2$ and $MnFe_xO_y$ would be 95:5. The particles of the Mn—Fe complex oxide ($MnFe_xO_y$) obtained by the aforementioned method (Mn/Fe atomic ratio 1:2, average particle diameter 4 µm, specific surface area 140 m²/g; 10 g) were added to 700 cc of an aqueous solution having 354 g of manganese nitrate hexahydrate dissolved therein. With stirring, 10% by weight of a KOH solution and 150 g of $KMnO_4$ were added, and stirring was continued for 1 hour. The resulting precipitate (a mixture of a $MnO_2$ precursor and $MnFe_xO_y$) was separated by a centrifugal separator, then washed with water, and then dried for 2 hours at 150° C. Then, the dried substance was fired for 3 hours at 350° C. in air to obtain catalyst 2 which was a mixture of $MnO_2$ and $MnFe_xO_y$ (weight ratio 95:5).

<<Preparation of Catalysts 3 to 7>>

Catalysts 3 to 7 were obtained in the same manner as for the catalyst 2, except that the proportions of the respective components were set at those shown in Table 1 in accordance with the catalyst 2.

<<Preparation of Catalyst 8>>

The $MnFe_xO_y$ mentioned above was used as catalyst 8.

<Average Coordination Number of Mn of Catalyst>

The resulting catalysts 1 to 5 and 8 were measured for the average coordination number of Mn—O [N(Mn—O)] by XAFS analysis shown below.

XAFS Analysis

The measurement of the XAFS spectrum was made using BL-12C of Photon Factory, High Energy Accelerator Research Organization. For analysis, least square fitting was performed on the absorption edge front region of the resulting spectrum $I_t/I_0$ with the use of Victoreen's calculation equation, and the result was extrapolated to subtract the background, followed by differentiation.

Average Coordination Number of Mn

Figure 2:
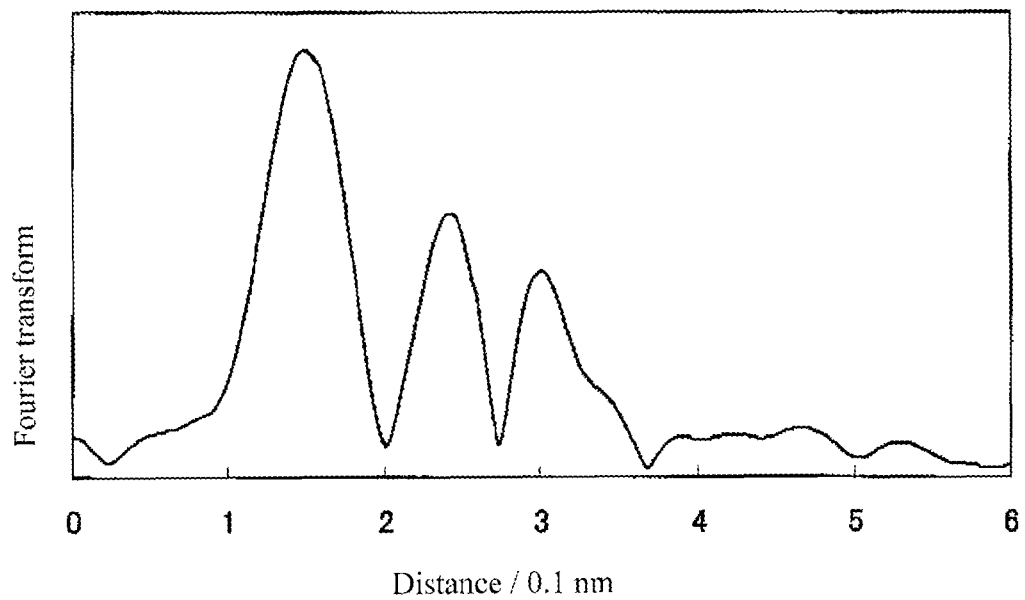
FIG. 2 shows the Fourier transform spectrum of EXAFS of Mn—K absorption edge of catalyst 3.

The average coordination number of Mn—O [N(Mn—O)] of each catalyst was analyzed by the following method: Fourier transformation was performed to obtain a radial structural function around the Mn atom, and a curve fitting was analyzed using REX-2000 (Rigaku Corporation). FIG. 2 shows the Fourier transform spectrum of Mn—K edge EXAFS measured at room temperature in air in connection with the catalyst 3 (phase shift was uncorrected). In the vicinity of 0.15, a peak due to contribution by Mn—O (primary coordination sphere) appeared. The analysis results on the [N(Mn—O)] in the catalyst based on the Fourier transform spectrum of the Mn—K edge EXAFS are shown in Table 1.

TABLE 1

| Catalyst | $MnO_2/MnFe_xO_y$ (weight ratio) | Average coordination number of Mn—O [N(Mn—O)] in catalyst |
|---|---|---|
| Catalyst 1 | 100/0 | 6.0 |
| Catalyst 2 (catalyst of the present invention) | 95/5 | 6.5 |
| Catalyst 3 (catalyst of the present invention) | 90/10 | 7.5 |
| Catalyst 4 (catalyst of the present invention) | 80/20 | 7.0 |
| Catalyst 5 (catalyst of the present invention) | 70/30 | 6.5 |
| Catalyst 6 | 50/50 | *** |
| Catalyst 7 | 10/90 | *** |
| Catalyst 8 | 0/100 | 6.0 |

Notes:
*** denotes no measured values.

As shown in Table 1, the average coordination numbers of Mn—O in the catalysts 2, 3, 4 and 5 obtained by mixing $MnO_2$ and the Mn—Fe complex oxide were 6.5 to 7.5, demonstrating clear increases over those of the catalyst 1 ($MnO_2$ alone) and the catalyst 8 ($MnFe_xO_y$ alone).

Example 2

Evaluation 1: Test for Removal of Acetaldehyde

A sample holder containing 0.5 g of a power of each of the catalysts prepared in Example 1 was fitted with a fan, and placed in a 30-liter container accommodating acetaldehyde adjusted to a concentration of 100 ppm. With the temperature inside the container being held at 25° C. and stirring with the fan being continued, changes in the concentration of the acetaldehyde in the container were measured by a photoacoustic gas monitor at intervals of 34 seconds over the course of 1 hour. The results are shown in Table 2 and FIG. 3. The catalysts composed of mixtures of $Fe_2O_3$ and Mn—Fe complex oxides introduced in the publicly known document 2 were subjected to the same evaluation, and the results are also shown as Referential Examples (catalysts 9, 10 and 11) in Table 2.

TABLE 2

| | Catalyst | $MnO_2$/ $MnFe_xO_y$, weight ratio | Residual concentration, ppm | | Removal rate, % | |
|---|---|---|---|---|---|---|
| | | | After 10 min | After 60 min | After 10 min | After 60 min |
| Comparative Example | Catalyst 1 | 100/0 | 90 | 75 | 10 | 25 |
| Example | Catalyst 2 | 95/5 | 62 | 30 | 38 | 70 |
| Example | Catalyst 3 | 90/10 | 53 | 20 | 47 | 80 |
| Example | Catalyst 4 | 80/20 | 52 | 16 | 48 | 84 |
| Example | Catalyst 5 | 70/30 | 56 | 25 | 44 | 75 |
| Comparative Example | Catalyst 6 | 50/50 | 70 | 47 | 30 | 53 |
| Comparative Example | Catalyst 7 | 10/90 | 80 | 67 | 20 | 33 |
| Comparative Example | Catalyst 8 | 0/100 | 82 | 68 | 18 | 32 |
| Referential Example | Catalyst 9 | $Fe_2O_3$/ $MnFe_xO_y$ (60/40) | 72 | 53 | 28 | 47 |
| Referential Example | Catalyst 10 | $Fe_2O_3$/ $MnFe_xO_y$ (80/20) | 87 | 75 | 13 | 25 |
| Referential Example | Catalyst 11 | $Fe_2O_3$ (100) | 99 | | 1 | |

Figure 3:
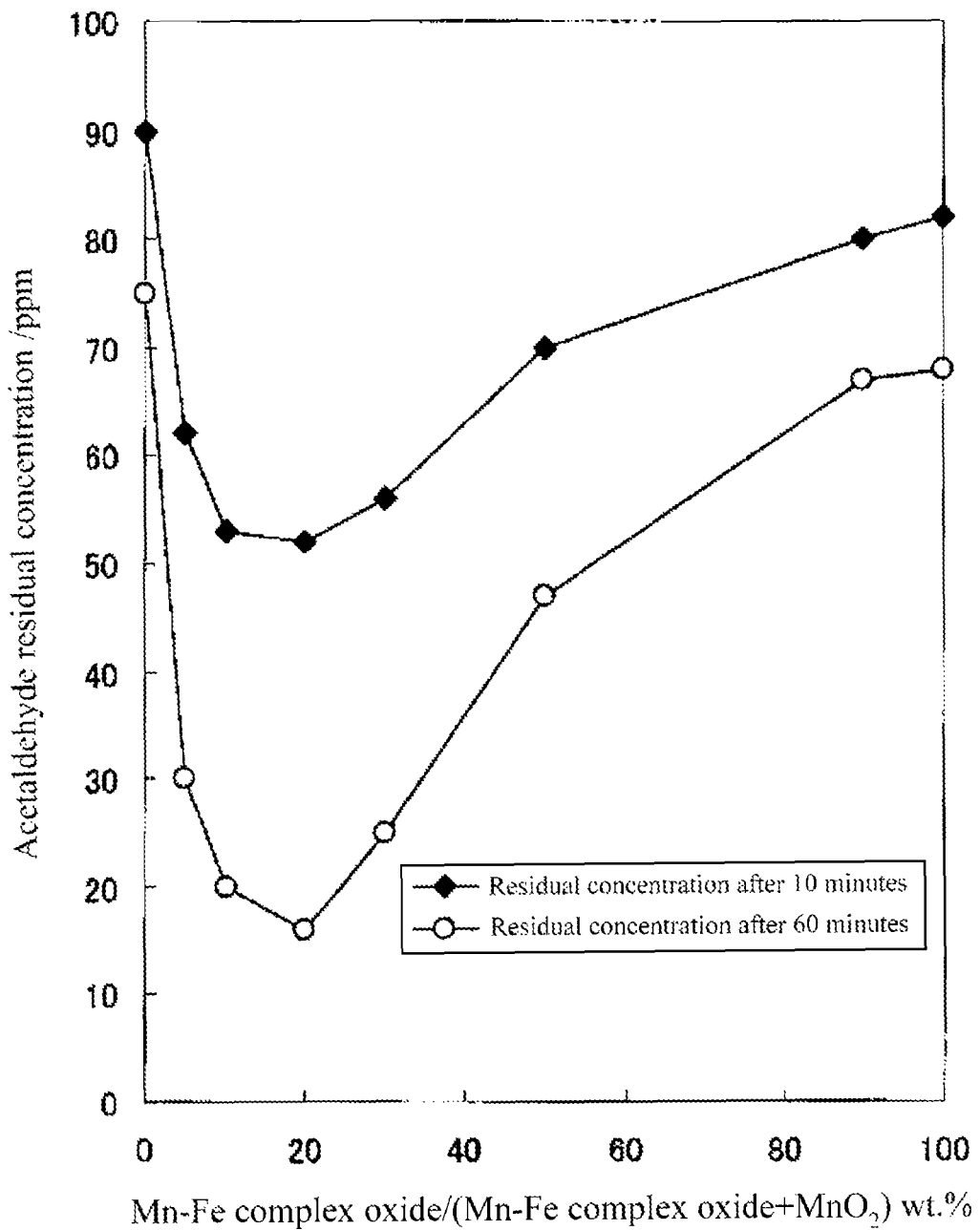
FIG. 3 shows the relationship between the proportion of the component 2 and deodorization performance.

As shown in Table 2 and FIG. 3, the catalysts 2 to 5 comprising manganese oxide and $MnFe_xO_y$ combined exhibit dramatically high deodorization rates in comparison with the catalyst composed of manganese oxide alone (catalyst 1) or the catalyst composed of $MnFe_xO_y$ alone (catalyst 8). In connection with each of the catalysts, reference to the average coordination number of Mn—O [N(Mn—O)] shown in Table 1 clearly shows that the catalysts 2, 3, 4 and 5 having a coordination number of 6.5 to 7.5 exhibit excellent deodorizing function. Clearly, the catalysts of the present invention have higher deodorization performance than do the deodorizing catalysts composed of a combination of iron oxide and Mn—Fe complex oxide shown in the aforementioned Patent Document 2 (i.e., catalysts 9 and 10). From FIG. 3, it is evident that the catalysts comprising the mixtures having a manganese oxide/$MnFe_xO_y$ weight ratio in the range of 98:2 to 60:40 are dramatically improved in the deodorizing action.

Example 3

Preparation of Honeycomb Catalyst

A honeycomb catalyst having the catalyst of the present invention carried on a honeycomb substrate was prepared by the following method:
Preparation of Slurry A composition as the catalyst 3 prepared in Example 1 was dispersed in water, and colloidal silica having a solids concentration of 20% was added as a binder to prepare a slurry A. Similarly, a composition as the catalyst 6 prepared in Example 1 was dispersed in water, and colloidal silica having a solids concentration of 20% was added as a binder to prepare a slurry B.

Moreover, manganese dioxide particles produced by treating manganese carbonate for 2 hours at 400° C. were dispersed in water, and colloidal silica having a solids concentration of 20% was added as a binder to prepare a slurry C.
Manufacture of Honeycomb Catalyst A corrugated honeycomb substrate (200 mm long, 200 mm wide, 15 mm thick, cell density: 80 cells per square inch) was rendered ready for use. The honeycomb substrate was dipped in each of the above slurry A, slurry B and slurry C, and then dried at 150° C. to prepare honeycomb catalysts A, B and C having 360 g/liter (including the binder) of the catalyst composition carried as a catalyst layer. The components of the respective honeycomb catalysts were as follows:

Honeycomb catalyst A (catalyst of the present invention): Manganese dioxide (90%)/$MnFe_xO_y$ (10%)

Honeycomb catalyst B (comparative catalyst): Manganese dioxide (50%)/$MnFe_xO_y$ (50%)

Honeycomb catalyst C (comparative catalyst): Manganese dioxide (100%)

Example 4

Evaluation 3: Flow-Through Test by Honeycomb Catalyst

Adsorption Capacity and One-Pass Removal Rate

The honeycomb catalyst produced in Example 3 (equipped with the fan) was installed in a cubic meter container having an acetaldehyde concentration adjusted to 4 ppm. With the temperature within the container being set at 25° C. and the speed of passage through the honeycomb catalyst being set at a wind velocity of 1.5 m/second (space velocity SV: 380,000 $hr^{-1}$), the acetaldehyde concentration inside the container was measured by a photoacoustic gas monitor at intervals of 34 seconds. At a time when the concentration reached a detection limit value or less (0.2 ppm), 4 ppm of acetaldehyde was further added into the container. This procedure was repeated a total of 3 times. At a time when the residual concentration of acetaldehyde lowered to 50% (2.0 ppm), all the amounts of acetaldehyde added were summed, and the total amount was taken as adsorption capacity. The adsorption capacity refers to the sum of the physically adsorbed content and the chemically adsorbed content. Based on changes (decays) in the concentration, the one-pass removal rate was calculated from Equation 1. The results of measurements of the adsorption capacity and the one-pass removal rate are shown in Table 3.

$$C = C1 \exp(-n\eta t)$$ [Equation 1]

where n denotes the number of ventilations (number of times/h), t denotes the elapsed time (hr), η denotes the one-pass removal rate (%), C denotes the concentration in the chamber (ppm), and C1 denotes the initial concentration.

TABLE 3

|  |  | $MnO_2/$ $MnFe_xO_y$ weight ratio | Adsorption capacity mg/cc, Note 2 | One-pass removal rate, % Note 1 |
|---|---|---|---|---|
| Example | Honeycomb catalyst A | 90/10 | 2.1 | 37 |
| Comparative Example | Honeycomb catalyst B | 50/50 | 0.4 | 24 |
| Comparative Example | Honeycomb catalyst C | 100/0 | 0.2 | 19 |

Note 1: Average value of 3 repeated measurements
Note 2: Amount of acetaldehyde adsorbed/cc of honeycomb catalyst As shown in Table 3, the one-pass removal rate of the honeycomb catalyst A of the present invention was 37%, representing a deodorization speed about 2 times as high as that of 19% of the honeycomb catalyst C having only $MnO_2$ carried thereon. The adsorption capacity of the honeycomb catalyst A of the present invention was 2.1 mg/cc, a value clearly about 10 times as great as that of the catalyst C, 0.2 mg/cc. The honeycomb catalyst having the deodorizing catalyst of the present invention carried thereon exhibited the performance that it purified air with an acetaldehyde concentration of 4 ppm down to 0.2 ppm or less. That is, the honeycomb catalyst exhibited a purifying action achieving the minimum achievable concentration which was a very low concentration.

Example 5

Using the honeycomb catalyst A and the honeycomb catalyst C shown in Example 4, their deodorization performance (adsorption capacity and one-pass removal rate) for acetic acid and ammonia was measured in the same manner as in Example 4. The results are shown in Table 4.

TABLE 4

|  | $MnO_2/$ $MnFe_xO_y$ weight ratio | Odorous components | Adsorption capacity mg/cc | One-pass removal rate, % |
|---|---|---|---|---|
| Honeycomb catalyst A | 90/10 | Acetic acid | 2.1 | 35 |
|  |  | Ammonia | 1.8 | 80 |
|  |  | Acetaldehyde | 2.1 | 37 |
| Honeycomb catalyst C | 100/0 | Acetic acid | *** | 20 |
|  |  | Ammonia | *** | 70 |
|  |  | Acetaldehyde | 0.2 | 11 |

Notes:
*** denotes no measured values.

As shown in Table 4, the honeycomb catalyst A of the present invention clearly has a high one-pass removal rate for ammonia and acetic acid as well as acetaldehyde, and has great adsorption capacity, in comparison with the honeycomb catalyst C, thus proving to be a catalyst having excellent deodorization performance.

Example 6

Evaluation of Regeneration Performance

The honeycomb catalyst A shown in Example 4 was allowed to adsorb 2.1 mg/cc of acetaldehyde. The catalyst A completing saturated adsorption was allowed to stand for 12 hours, and then heated for 30 minutes at 150° C. in an air atmosphere within the container. Then, its one-pass removal rate for acetaldehyde was measured by the method shown in Example 4. The results are shown in Table 5.

TABLE 5

| No. of | One-pass removal rate, % | |
|---|---|---|
| times | New product | After regeneration |
| 1 | 37 | 36 |
| 2 | 37 | 37 |
| 3 | 36 | 36 |

Table 5 clearly shows that the honeycomb catalyst A can be regenerated nearly completely upon heating at 150° C.

Example 7

Evaluation of Pressure Loss and Deodorization Rate of Honeycomb Catalyst

Using the catalyst of the present invention, a preferred combination of the cell density of the honeycomb and the amount carried, designed to suppress an increase in the pressure loss and maximize the one-pass efficiency during high speed treatment of a large amount of air, was investigated as described below.

The slurry A shown in Example 3 was used on three corrugated honeycomb substrates having a cell density of 30 cells/square inch (honeycomb 1), 56 cells/square inch (honeycomb 2), and 80 cells/square inch (honeycomb 3), and honeycomb catalysts having the catalyst compositions carried in amounts within the range of 200 to 480 g per liter were prepared by the method shown in Example 3.

Measurement of Pressure Loss

The honeycomb catalyst was mounted in a duct having a section of 62×62 mm and a length of 1000 mm. Air at an acetaldehyde concentration of 4 ppm was flowed through the catalyst at a wind velocity of 3.5 m/second. The total pressures at the inlet and outlet of the catalyst were measured, and a pressure difference between the total pressures was taken as a pressure loss. At the same time, the one-pass removal rate was measured by the method shown in Example 4.

Figure 4:
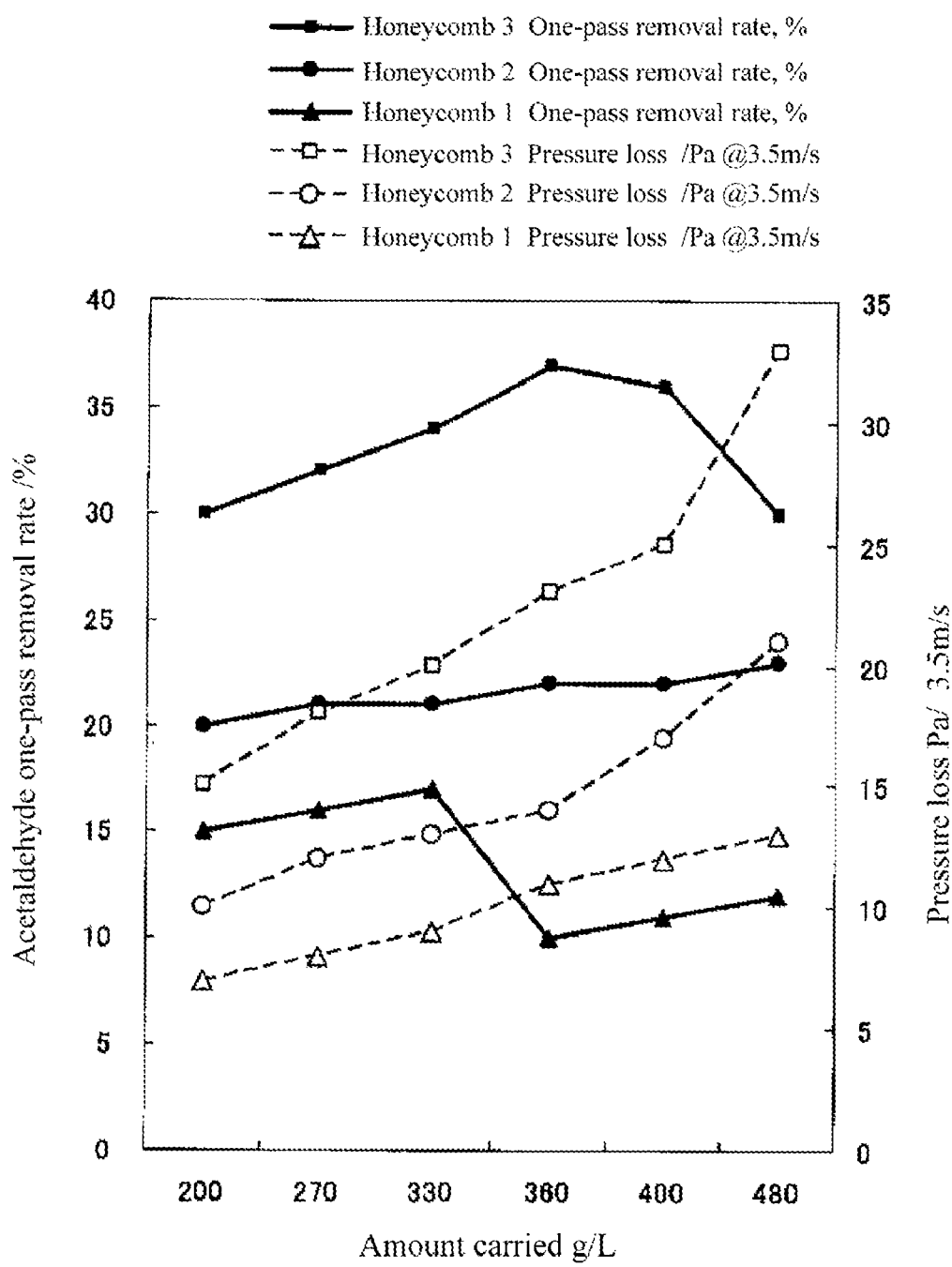
FIG. 4 shows the relationship among the amount of the catalyst carried, the one-pass removal rate, and the pressure loss.

The results of the deodorization treatment using the honeycomb catalysts involving the different combinations of the cell density of the honeycomb and the amount of the catalyst carried are shown in Table 6 and FIG. 4.

TABLE 6

| | Honeycomb 1 30 cells/in² | | Honeycomb 2 56 cells/in² | | Honeycomb 3 80 cells/in² | |
|---|---|---|---|---|---|---|
| Amount carried g/L | Pressure loss/Pa @3.5 m/sec | One-pass removal rate/% | Pressure loss/Pa @3.5 m/sec | One-pass removal rate/% | Pressure loss/Pa @3.5 m/sec | One-pass removal rate/% |
| 200 | 7 | 15 | 10 | 20 | 15 | 30 |
| 270 | 8 | 16 | 12 | 21 | 18 | 32 |
| 330 | 9 | 17 | 13 | 21 | 20 | 34 |
| 360 | 11 | 10 | 14 | 22 | 23 | 37 |
| 400 | 12 | 11 | 17 | 22 | 25 | 36 |
| 480 | 13 | 12 | 21 | 23 | 33 | 30 |

As shown in Table 6, with the same amount carried, the greater the cell density, the higher the one-pass removal rate becomes, but the problem arises that the pressure loss increases. On the other hand, an increase in the amount carried does not necessarily mean an increase in the one-pass removal rate. With the honeycomb 1 (cell density: 30), the removal rate decreases, with the amount carried of 330 g/liter providing the highest removal rate. With the honeycomb 2 (cell density: 56), the removal rate scarcely changes, even when the amount carried is changed.

It is clear that in order to obtain a honeycomb catalyst having a one-pass removal rate of 25% or more, with a pressure loss of 40 Pa or less, under high speed conditions expressed as a wind velocity of 3.5 m/second, the catalyst of the present invention is carried in an amount of 200 to 500 g/liter on a honeycomb substrate having a cell density of 80, whereby this object can be attained.

It is also clear, as shown in FIG. 4, that in order to obtain a honeycomb catalyst having a one-pass removal rate of 30% or more, with a pressure loss of 30 Pa or less, at a treatment speed expressed as a wind velocity of 3.5 m/second, the catalyst of the present invention is carried in an amount of 200 to 450 g/liter on a honeycomb substrate having a cell density of 70 to 80 cells/square inch, whereby the intended object can be attained. If the wind velocity is 3.0 m/second, the pressure loss decreases further, and the one-pass removal rate increases. Thus, it is clear that the desired honeycomb catalyst can be attained by carrying the catalyst of the present invention in an amount of 200 to 500 g/liter on a honeycomb substrate having a cell density of 50 to 100 cells/square inch. Incidentally, the wind velocity of 3.5 m/second corresponds to the space velocity (SV) of 830,000 hr$^{-1}$, and the wind velocity of 3.0 m/second corresponds to SV of 714,000 hr$^{-1}$. The achievement of the one-pass removal rate of 30% or higher, not to mention 25% or higher, under such high speed conditions and at room temperature, means that the deodorization performance of the catalyst of the present invention is extremely high.

Example 8

Na-MFI40 zeolite (Na ion-substituted MFI type zeolite, SiO$_2$/Al$_2$O$_3$ molar ratio: 38) was mixed, at a ratio of 67:33, with the catalysts 1 to 8 prepared in Example 1 to prepare powdery catalysts A1 to A8.

<Evaluation 1: Test for Removal of Acetaldehyde>

The deodorizing effect of the resulting respective catalyst powders on acetaldehyde was investigated by the method of <Evaluation 1: Test for removal of acetaldehyde> shown in Example 2. The results are shown in Table 7.

TABLE 7

| | | Composition of catalyst | | Residual concentration, ppm | |
|---|---|---|---|---|---|
| | | Composition of manganese oxide used | MO composition/ zeolite weight ratio | After 10 min | After 60 min |
| Comp. Ex. | Catalyst A1 | MO composition 1 | 67:33 | 72 | 62 |
| Ex. | Catalyst A2 | MO composition 2 | 67:33 | 63 | 45 |
| Ex. | Catalyst A3 | MO composition 3 | 67:33 | 60 | 37 |
| Ex. | Catalyst A4 | MO composition 4 | 67:33 | 57 | 30 |
| Ex. | Catalyst A5 | MO composition 5 | 67:33 | 61 | 39 |
| Comp. Ex. | Catalyst A6 | MO composition 6 | 67:33 | 65 | 50 |
| Comp. Ex. | Catalyst A7 | MO composition 7 | 67:33 | 67 | 56 |
| Comp. Ex. | Catalyst A8 | MO composition 8 | 67:33 | 69 | 60 |

As shown in Table 7, it is clear that the catalysts A2 to A5 of the present invention comprising manganese oxide, Mn—Fe complex oxide and zeolite exhibit a markedly increased deodorization speed, as compared with the catalyst A1 containing no Mn—Fe complex oxide and composed of manganese oxide and zeolite (comparative example).

In view of the relation of the MO composition, which is a constituent of the catalysts A1 to A8, to the average coordination number of Mn—O [N(Mn—O)] (Table 1), it is evident that the catalysts A2, A3, A4 and A5 containing the manganese oxide composition having N(Mn—O) of 6.5 to 7.5 exhibit particularly satisfactory deodorizing function.

Example 9

Test for Deodorization of Hydrogen Sulfide, Organic Sulfur Compounds and Organic Nitrogen Compounds Using the testing devices shown in Example 2, hydrogen sulfide, methyl mercaptan, and trimethylamine, instead of acetaldehyde, were charged into the container at an initial concentration of 100 ppm, and subjected to a deodorization test with the use of the catalyst A2 prepared in Example 8. The residual concentrations after 10 minutes and 60 minutes are shown in Table 8. The catalyst of the present invention exhibited a deodorizing effect on the respective odor components.

TABLE 8

| Odor component | Residual concentration, ppm | |
|---|---|---|
| | After 10 min | After 60 min |
| Hydrogen sulfide | 3 | 0 |
| Methyl mercaptan | 27 | 0.32 |
| Trimethylamine | 24 | 0 |

Example 10

Preparation of Honeycomb Catalysts C1 to C18

The MO compositions 1 to 6 shown in Table 7 were combined with various zeolites to prepare slurries by the method shown in Example 3. Each of the slurries was carried, as 200 g/L of a catalyst layer, on the honeycomb substrate to produce honeycomb catalysts C1 to C18 listed in Table 9.

The zeolites used were as follows:
Na-MFI40 (Na ion-substituted MFI type, $SiO_2/Al_2O_3$ molar ratio: 38)
$NH_4$-MFI95 (ammonium ion-substituted MFI type zeolite, $SiO_2/Al_2O_3$ ratio: 95)
H-MFI95 (proton-substituted MFI type zeolite, $SiO_2/Al_2O_3$ ratio: 95)
β (beta type zeolite, $SiO_2/Al_2O_3$ ratio: 35)
H-MFI1000 (proton-substituted MFI type zeolite, $SiO_2/Al_2O_3$ ratio: 480) Na—Y (Na ion-substituted Y type zeolite, $SiO_2/Al_2O_3$ ratio: 3)

TABLE 10

| | Honeycomb catalyst | Adsorption capacity, mg/cc, Note 2 | One-pass removal rate (%), Note 1 |
|---|---|---|---|
| Comp. Ex. | C1 | 0.2 | 19 |
| Comp. Ex. | C2 | 0.5 | 21.3 |
| Comp. Ex. | C3 | 0.7 | 24.0 |
| Comp. Ex. | C4 | 1.3 | 28.5 |
| Ex. | C5 | 1.6 | 40.5 |
| Comp. Ex. | C6 | 2.1 | 37 |
| Ex. | C7 | 1.8 | 42.0 |
| Comp. Ex. | C8 | *** | 35 |
| Ex. | C9 | 1.8 | 39.5 |
| Comp. Ex. | C10 | *** | 31 |
| Ex. | C11 | 1.4 | 35 |
| Comp. Ex. | C12 | 0.4 | 24 |
| Comp. Ex. | C13 | 1.1 | 28.3 |
| Ex. | C14 | 2.1 | 32 |
| Ex. | C15 | 1.8 | 32 |
| Ex. | C16 | 1.5 | 20 |
| Ex. | C17 | 1.3 | 13 |
| Ex. | C18 | 1.2 | 15 |

Note 1: Average value of 3 repeated measurements
Note 2: *** denotes no measured values.

Table 10 shows the following findings:
(1) The catalysts of the present invention containing Mn—Fe complex oxides, as compared with the catalysts free of the complex oxides (for example, C1 and C2), have great adsorption capacity and have high one-pass removal rates, thus proving to have high deodorizing power (speed and durability).
(2) The catalysts of the present invention containing zeolite (for example C5, C7), as compared with the catalysts of the

TABLE 9

| | Honeycomb catalyst | MO composition Note 1 | $MnO_2/MnFe_xO_y$ Weight ratio | Zeolite (Z) | MO/Z Weight ratio, Note 2 |
|---|---|---|---|---|---|
| Comp. Ex. | C1 | 1 | 100/0 | None | 100/0 |
| Comp. Ex. | C2 | 1 | 100/0 | Na-MFI40 | 67/33 |
| Comp. Ex. | C3 | 8 | 0/100 | Na-MFI40 | 67/33 |
| Comp. Ex. | C4 | 2 | 95/5 | None | 100/0 |
| Ex. | C5 | 2 | 95/5 | Na-MFI40 | 67/33 |
| Comp. Ex. | C6 | 3 | 90/10 | None | 100/0 |
| Ex. | C7 | 3 | 90/10 | Na-MFI40 | 67/33 |
| Comp. Ex. | C8 | 4 | 80/20 | None | 100/0 |
| Ex. | C9 | 4 | 80/20 | Na-MFI40 | 67/33 |
| Comp. Ex. | C10 | 5 | 70/30 | None | 100/0 |
| Ex. | C11 | 5 | 70/30 | Na-MFI40 | 67/33 |
| Comp. Ex. | C12 | 6 | 50/50 | None | 100/0 |
| Comp. Ex. | C13 | 6 | 50/50 | Na-MFI40 | 67/33 |
| Ex. | C14 | 3 | 90/10 | NH4-MFI95 | 67/33 |
| Ex. | C15 | 3 | 90/10 | H-MFI95 | 67/33 |
| Ex. | C16 | 3 | 90/10 | β | 67/33 |
| Ex. | C17 | 3 | 90/10 | H-MFI1000 | 67/33 |
| Ex. | C18 | 3 | 90/10 | Na—Y | 67/33 |

Note 1: The numbers assigned to the MO compositions agree with the numbers in Table 1.
Note 2: MO represents the total weight of manganese oxide and Mn—Fe complex oxide, and Z represents the weight of zeolite.

Example 11

In connection with the honeycomb catalysts C1 to C18 prepared in Example 10, the one-pass removal rate and the adsorption capacity were measured by the methods shown in Example 4. The results of the measurements are shown in Table 10.

Comparative Examples free of zeolite (for example, C4, C6), markedly increase in the one-pass removal rate.
(3) Any of the catalysts using the MFI type, β type and Y type as zeolite (for example, C5, C16, C18) had adsorption capacity about 2 to 4 times as great as that of the publicly known catalyst (for example, C2). Of them, the catalysts using MFI type zeolites having a $SiO_2/Al_2O_3$ molar ratio of 38 and 95 (for example, C5, C14, C15) exhibited excellent effects in both of the adsorption capacity and the one-pass removal rate.

Example 12

Evaluation 4: Evaluation of Deodorization of Tobacco Smell

The honeycomb catalysts C6 and C7 shown in Example 10 were each cut to a size of 53 mm in length and 45 mm in width, and used for evaluation of tobacco deodorization performance in the following manner:
<Method of Measurement>
The honeycomb catalyst mounted on a deodorization device was installed in a 57-liter deodorization box, and then tobacco smoke generated by a smoking implement was filled into the box for 5 seconds. Then, the initial concentrations of the odor components were measured. Then, the fan of the deodorization device was actuated to carry out deodorization treatment for 30 minutes, and the concentrations after treatment were measured. Air inside the box was changed by ventilation, and then the same procedure was repeated 7 times. The measurements of the concentrations were made during the odd-numbered runs of the 7 runs having performed the same procedure. The results of the measurements of the removal rates for acetaldehyde, acetic acid and ammonia components are shown in Table 11.

TABLE 11

| | Zeolite content | $MnO_2$/$MnFe_xO_y$ Weight ratio | Odor component | Removal rate, % | | | |
|---|---|---|---|---|---|---|---|
| | | | | 1st run | 3rd run | 5th run | 7th run |
| Honeycomb catalyst C6 | 0% | 90/10 | Acetaldehyde | 100 | 100 | 88 | 57 |
| | | | Acetic acid | 80 | 87 | 75 | 76 |
| | | | Ammonia | 100 | 100 | 100 | 100 |
| Honeycomb catalyst C7 | 33% | 90/10 | Acetaldehyde | 100 | 100 | 100 | 68 |
| | | | Acetic acid | 82 | 87 | 88 | 88 |
| | | | Ammonia | 100 | 100 | 100 | 100 |

As shown in Table 11, the catalyst C6 free of zeolite began to decrease in the removal rate for acetaldehyde from the 5th run onward, and its removal rate for acetic acid similarly decreased. On the other hand, the honeycomb catalyst C7 of the present invention containing zeolite was persistent in showing a high removal rate for each component even after repeated treatment. The catalyst of the present invention is clearly capable of removing a plurality of odor components simultaneously.

Example 13

Honeycomb Catalysts B1 to B8

Using the MO composition 3 shown in Table 7, zeolite was mixed with it to prepare honeycomb catalysts B1 to B8 shown in Table 12.
Preparation of Catalyst Slurry
<<Catalyst Slurry B1>>
The MO composition 3 was dispersed in water, and colloidal silica (solids concentration: 20% by weight) was added as a binder to prepare a catalyst slurry B1 containing 85% by weight of particles of the MO composition 3.
<Catalyst Slurry B2>
The MO composition 3 and Na-MFI40 (Na ion-substituted MFI type, $SiO_2/Al_2O_3$ molar ratio: 38) as zeolite were dispersed at a weight ratio of 90:10 in water, and the above-mentioned binder was added to prepare a catalyst slurry B2 containing a total of 85% by weight of the MO composition 3 and zeolite.
<<Catalyst Slurries B3 to B7>>
Catalyst slurries B3 to B7 were prepared by the same method as for the catalyst slurry B2, except that the ratio between the MO composition 3 and the above zeolite was changed.
<<Catalyst Slurry B8>>
A catalyst slurry B8 containing 85% by weight of the above zeolite particles and the above binder was prepared in the same manner as described above.
Preparation of Honeycomb Catalyst
A corrugated honeycomb (200 mm long, 200 mm wide, 15 mm thick, cell density: 80 cells per square inch) was rendered ready for use. The honeycomb was dipped in each of the above catalyst slurries B1 to B8, and then dried at 220° C. to prepare honeycomb catalysts B1 to B8 having 200 g/liter of each catalyst composition carried as a catalyst layer.
<Test for Removal of Acetaldehyde>
The one-pass removal rate of the honeycomb catalysts B1 to B8 for acetaldehyde was calculated based on the method and the Equation 1 shown in Example 4. Further, the time until the acetaldehyde concentration inside the container reached a detection limit value or less (0.2 ppm) (called 100% removal time) was measured. The results of the evaluations performed using each honeycomb catalyst are shown in Table 12 and FIG. 5.

TABLE 12

| | Honeycomb catalyst | MO composition 3/zeolite Weight ratio | One-pass removal rate, % | 100% removal time, min |
|---|---|---|---|---|
| Comp. Ex. | B1 | 100:0 | 30 | 4.3 |
| Ex. | B2 | 90:10 | 32 | 6.0 |
| Ex. | B3 | 80:20 | 34 | 6.5 |
| Ex. | B4 | 67:33 | 37 | 6.5 |
| Ex. | B5 | 60:40 | 37 | 10 |
| Ex. | B6 | 50:50 | 36 | 25 |
| Ex. | B7 | 33:67 | 37 | 45 |
| Comp. Ex. | B8 | 0:100 | 34.5 | 100 |

Figure 5:
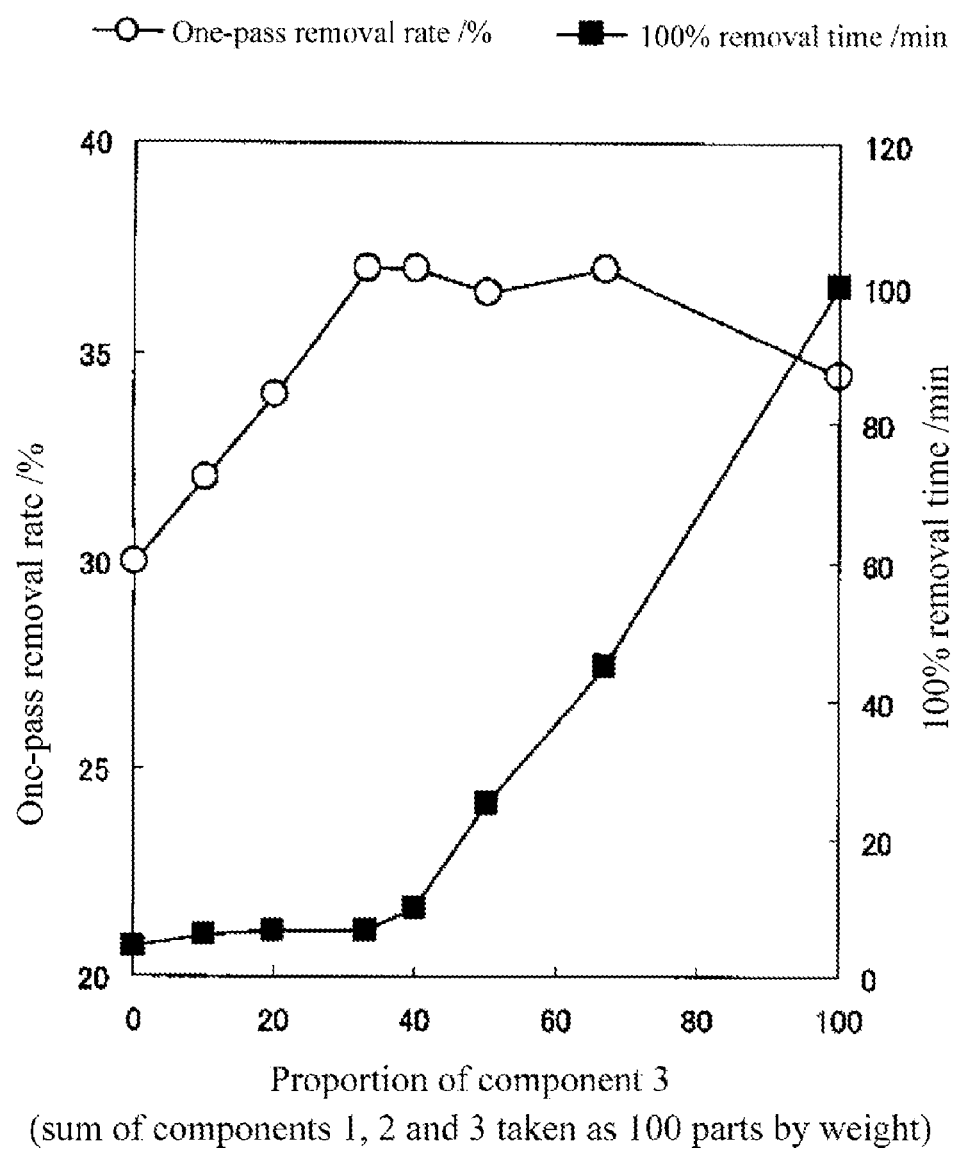
FIG. 5 shows the relationship between the proportion of the component 3 and deodorization performance, provided that the proportions of the component 1, the component 2 and the component 3 total 100 parts by weight.

As shown in Table 12 and FIG. 5, it is clear that the honeycomb catalysts containing zeolite in proportions (notes: the total weight of the component 1, the component 2 and the component 3 is taken as 100) of 10 to 60%, particularly 10 to 50%, especially 20 to 50%, have a high one-pass removal rate and can maintain the 100% removal time short.

Example 14

Deodorizing Catalyst Containing Potassium

A powder (5 g) of the catalyst 4 shown in Example 1 ($MnO_2/MnFe_xO_y$ weight ratio: 80/20) was impregnated with 10 g of an aqueous solution having 0.05 g of $K_2CO_3$ dissolved therein, followed by drying at 150° C., to prepare a potassium-containing deodorizing catalyst K1 shown in Table 13. Using the aqueous solution with the amount of $K_2CO_3$ varied, deodorizing catalysts K2 to K6 were prepared by the same method as above.
<Evaluation: Test for Removal of Acetaldehyde>
Using the catalysts K1 to K7, a test for removal of acetaldehyde was conducted by the method shown in Example 2. The results are shown in Table 13.

TABLE 13

| Catalyst | | K content, wt. % (as K$_2$O) | Residual concentration, ppm | | Removal rate, % | |
|---|---|---|---|---|---|---|
| | | | After 10 min | After 60 min | After 10 min | After 60 min |
| Catalyst 4 | MnO$_2$/ MnFe$_x$O$_y$ (80/20) | 0 | 52 | 16 | 48 | 84 |
| Catalyst K1 | K carried on catalyst 4 | 0.7 | 49 | 12 | 51 | 88 |
| Catalyst K2 | Ditto | 1.0 | 46 | 10 | 54 | 90 |
| Catalyst K3 | Ditto | 1.4 | 44 | 9 | 56 | 91 |
| Catalyst K4 | Ditto | 1.8 | 45 | 11 | 55 | 89 |
| Catalyst K5 | Ditto | 2.1 | 50 | 15 | 50 | 85 |
| Catalyst K6 | Ditto | 3.5 | 58 | 22 | 42 | 78 |

As shown in Table 13, the deodorizing catalysts of the present invention containing potassium were further improved in the removal speed of the acetaldehyde component.

Example 15

Using the power as the catalyst K3 shown in Example 14, a honeycomb catalyst D1 (cell density: 80 cells/square inch) having the potassium-containing catalyst of the present invention provided as a catalyst layer (amount carried: 360 g/L) was produced by the method shown in Example 3.

<Measurement of Adsorption Capacity and One-Pass Removal Rate for Acetaldehyde>

The adsorption capacity and one-pass removal rate of the honeycomb catalyst D1 for acetaldehyde were measured by the methods shown in Example 4. The results are shown in Table 14 in comparison with the results on the potassium-free catalyst A (the aforementioned Table 5).

TABLE 14

| | MnO$_2$/ MnFe$_x$O$_y$ weight ratio | K content, wt. % (as K20) | Adsorption capacity, mg/cc | One-pass removal rate, % |
|---|---|---|---|---|
| Honeycomb catalyst D | 80/20 | 1.4 | 2.7 | 40 |
| Honeycomb catalyst A | 90/10 | Not contained | 2.1 | 37 |

As shown in Table 14, it is clear that the incorporation of potassium further increases the adsorption capacity and one-pass removal rate of the catalyst of the present invention.

The invention claimed is:

1. A deodorizing catalyst composition comprising manganese oxide (component 1) and a complex oxide of manganese and iron (component 2) at a weight ratio in a range of 98:2 to 60:40.

2. The deodorizing catalyst composition according to claim 1, wherein the weight ratio between the component 1 and the component 2 is 98:2 to 70:30.

3. The deodorizing catalyst composition according to claim 1, wherein an average coordination number of Mn—O [N(Mn—O)] of a mixture of the component 1 and the component 2 is 6.5 to 7.5.

4. The deodorizing catalyst composition according to claim 1, further comprising zeolite (component 3), and wherein a weight ratio of a total amount of the component 1 and the component 2 to an amount of the component 3 is 90:10 to 50:50.

5. The deodorizing catalyst composition according to claim 4, wherein the component 3 is zeolite having a SiO$_2$/Al$_2$O$_3$ molar ratio of 3 to 100.

6. The deodorizing catalyst composition according to claim 4, wherein the component 3 is one or more of MFI-type zeolite, β-type zeolite, and mordenite-type zeolite.

7. The deodorizing catalyst composition according to claim 1, further comprising potassium (component 4).

8. The deodorizing catalyst composition according to claim 7, wherein a content of the component 4, expressed based on potassium oxide, is 0.1 to 3% by weight with respect to a sum of the component 1 and the component 2.

9. The deodorizing catalyst composition according to claim 7, wherein the component 4 is incorporated by impregnating particles of at least one of the component 1 and the component 2 with a solution of a potassium compound, and then drying the impregnated particles at a temperature of 250° C. or lower, thereby impregnating the particles of at least one of the component 1 and the component 2 with the potassium compound or potassium oxide.

10. The deodorizing catalyst composition according to claim 9, wherein the potassium compound is one or more compounds selected from inorganic acid salts, organic acid salts, and hydroxides.

11. The deodorizing catalyst composition according to any one of claims 1 to 10, adapted to remove one or more components to be deodorized, among acetaldehyde, tobacco smell components, formaldehyde, acetic acid, ammonia, volatile organic nitrogen compounds, hydrogen sulfide, and volatile organic sulfur compounds.

12. A method for producing the deodorizing catalyst composition according to any one of claims 7 to 10, comprising:
 a step 1 of impregnating mixed particles, which contain the component 1 and the component 2 at a weight ratio in a range of 98:2 to 60:40, with a solution of a potassium compound; and
 a step 2 of drying the impregnated mixed particles at a temperature of 250° C. or lower.

13. A deodorizing catalyst comprising the deodorizing catalyst composition according to claim 1 carried on a catalyst substrate.

14. The deodorizing catalyst according to claim 13, wherein the catalyst substrate is a honeycomb substrate having a cell density of 50 to 100 cell/square inch, and which has the deodorizing catalyst composition carried on the substrate as a catalyst layer in an amount of 200 to 500 g/L.

15. A method for producing the deodorizing catalyst according to claims 13 or 14, comprising:
 a step 1 of coating the catalyst substrate with a slurry containing the component 1, the component 2 and a potassium compound; and
 a step 2 of drying the coated catalyst substrate at a temperature of 250° C. or lower.

16. A method for producing the deodorizing catalyst according to claims 13 or 14, comprising:
 a step 1 of coating the catalyst substrate with a slurry containing the component 1 and the component 2;
 a step 2 of impregnating the coated catalyst substrate with a solution of a potassium compound; and
 a step 3 of drying the impregnated catalyst substrate at a temperature of 250° C. or lower.

17. A deodorizing method, comprising:
 passing air, as an object to be treated, through the deodorizing catalyst according to claims 13 or 14 at a flow velocity of 0.5 to 4.0 m/second, the air containing one or more of acetaldehyde, tobacco smell components, formaldehyde, acetic acid, ammonia, volatile organic nitrogen compounds, hydrogen sulfide, and volatile organic sulfur compounds.

18. A method for regenerating a deodorizing catalyst composition, comprising:
heating the deodorizing catalyst composition according to any one of claims 1 to 10 to 140° C.-250° C. in an air atmosphere, the deodorizing catalyst composition having adsorbed thereto one or more of acetaldehyde, tobacco smell components, formaldehyde, acetic acid, ammonia, sulfur compounds, and organic nitrogen compounds, which are odor components.

19. A method for regenerating a deodorizing catalyst, comprising:
heating the deodorizing catalyst according to claims 13 or 14 to 140° C.-250° C. in an air atmosphere, the deodorizing catalyst having adsorbed thereto one or more of acetaldehyde, tobacco smell components, formaldehyde, acetic acid, ammonia, sulfur compounds, and organic nitrogen compounds, which are odor components.

* * * * *